（12) United States Patent
Göbel (10) Patent No.: US 11,324,932 B2
(45) Date of Patent: May 10, 2022

(54) TRANS-ANAL INFLOW CATHETER FOR INTERMITTENTLY TRIGGERING A REFLEX-COORDINATED DEFECATION

(71) Applicant: Fred Göbel, Wilhelmsfeld (DE)

(72) Inventor: Fred Göbel, Wilhelmsfeld (DE)

(73) Assignee: Advanced Medical Balloons GmbH, Waghäusel (DE)

( * ) Notice: Subject to any disclaimer, the term of this patent is extended or adjusted under 35 U.S.C. 154(b) by 392 days.

(21) Appl. No.: 16/026,889

(22) Filed: Jul. 3, 2018

(65) Prior Publication Data

US 2018/0311481 A1 Nov. 1, 2018

Related U.S. Application Data

(63) Continuation-in-part of application No. 14/239,991, filed as application No. PCT/EP2012/003535 on Aug. 20, 2012, now abandoned.

(30) Foreign Application Priority Data

| Aug. 20, 2011 | (DE) | ...................... | 10 2011 111 225.5 |
| Nov. 21, 2011 | (DE) | ...................... | 10 2011 118 943.6 |
| Dec. 16, 2011 | (DE) | ...................... | 10 2011 121 202.0 |
| Mar. 22, 2012 | (DE) | ...................... | 10 2012 005 607.9 |
| Apr. 25, 2012 | (DE) | ...................... | 10 2012 008 361.0 |

(51) Int. Cl.
*A61M 25/00* (2006.01)
*A61M 25/10* (2013.01)
(Continued)

(52) U.S. Cl.
CPC ....... *A61M 25/1002* (2013.01); *A61F 2/0013* (2013.01); *A61M 3/0295* (2013.01); *A61M 25/0662* (2013.01); *A61M 25/1029* (2013.01); *A61M 25/10186* (2013.11); *A61M 3/0262* (2013.01); *A61M 25/09041* (2013.01);
(Continued)

(58) Field of Classification Search
CPC ........ A61M 25/09041; A61M 25/1009; A61M 25/10188; A61M 25/10181; A61M 25/1029; A61M 25/0662; A61M 25/10186; A61M 25/1002; A61M 2025/09116; A61M 2025/0687; A61M 2025/1052;
(Continued)

(56) References Cited

U.S. PATENT DOCUMENTS

| 2,610,626 A | 9/1952 | Edwards |
| 3,939,842 A | 2/1976 | Harris |
(Continued)

FOREIGN PATENT DOCUMENTS

| DE | 102004033425 | 7/2006 |
| DE | 102009008594 | 8/2010 |
(Continued)

*Primary Examiner* — Nathan R Price
*Assistant Examiner* — Anh Bui
(74) *Attorney, Agent, or Firm* — Pandiscio & Pandiscio (57) ABSTRACT

The invention relates to a device for transanally introducing an infusion into the rectum or colon of a patient, said device comprising a catheter with a catheter shaft wherein, to ensure the most practicable catheter insertion possible, the catheter shaft is equipped in the proximal, preanal region with gripping depressions to accommodate the fingers gripping the catheter during insertion.

35 Claims, 8 Drawing Sheets

(51) Int. Cl.
   *A61F 2/00* (2006.01)
   *A61M 25/06* (2006.01)
   *A61M 3/02* (2006.01)
   *A61M 25/09* (2006.01)

(52) U.S. Cl.
   CPC ... *A61M 25/1009* (2013.01); *A61M 25/10181* (2013.11); *A61M 25/10188* (2013.11); *A61M 2025/0687* (2013.01); *A61M 2025/09116* (2013.01); *A61M 2025/1052* (2013.01); *A61M 2210/1064* (2013.01); *A61M 2210/1067* (2013.01)

(58) Field of Classification Search
   CPC .. A61M 2210/1067; A61M 2210/1064; A61M 3/0262; A61M 3/0295; A61F 2/0013
   See application file for complete search history.

(56) References Cited

U.S. PATENT DOCUMENTS

| | | | |
|---|---|---|---|
| 4,403,982 A * | 9/1983 | Clayton | A61M 3/0241 604/28 |
| 4,555,242 A | 11/1985 | Saudagar | |
| 5,125,916 A | 6/1992 | Panebianco et al. | |
| 7,122,025 B1 * | 10/2006 | Nestenborg | A61F 5/451 604/540 |
| 9,339,442 B2 | 5/2016 | Tai et al. | |
| 2003/0220621 A1 * | 11/2003 | Arkinstall | A61F 5/445 604/335 |
| 2003/0236183 A1 | 12/2003 | De Bruijn et al. | |
| 2007/0021651 A1 | 1/2007 | Gobel | |
| 2007/0027520 A1 | 2/2007 | Sherburne | |
| 2007/0213661 A1 * | 9/2007 | Gobel | A61F 2/0013 604/96.01 |
| 2009/0036945 A1 | 2/2009 | Chancellor et al. | |
| 2009/0171278 A1 * | 7/2009 | Hirszowicz | A61B 17/22012 604/97.01 |
| 2010/0087792 A1 | 4/2010 | Nielsen et al. | |
| 2011/0160657 A1 | 6/2011 | Göbel | |
| 2011/0218389 A1 | 9/2011 | Göbel | |
| 2014/0276631 A1 | 9/2014 | Gilman | |
| 2014/0336569 A1 | 11/2014 | Göbel | |

FOREIGN PATENT DOCUMENTS

| | | |
|---|---|---|
| EP | 0504090 A1 | 9/1992 |
| FR | 2480127 | 10/1981 |
| JP | 3-116847 | 12/1991 |
| JP | 10-234854 | 9/1998 |
| JP | 2014-524293 | 9/2014 |
| UA | 68194 A | 7/2004 |
| WO | WO 2006/010556 | 2/2006 |
| WO | WO 2007/118621 | 10/2007 |
| WO | WO 2008/103788 | 8/2008 |
| WO | WO 2011/012323 | 2/2011 |

* cited by examiner

TRANS-ANAL INFLOW CATHETER FOR INTERMITTENTLY TRIGGERING A REFLEX-COORDINATED DEFECATION

REFERENCE TO PENDING PRIOR PATENT APPLICATIONS

This patent application is a continuation-in-part of pending prior U.S. patent application Ser. No. 14/239,991, filed Feb. 20, 2014 by Fred Göbel for TRANS-ANAL INFLOW CATHETER AND METHOD FOR INTERMITTENTLY TRIGGERING A REFLEX-COORDINATED DEFECATION (Attorney's Docket No. KUCH-59), which in turn is a 371 national stage entry of International (PCT) Patent Application No. PCT/EP2012/003535, filed Aug. 20, 2012 by Fred Göbel for TRANS-ANAL INFLOW CATHETER AND METHOD FOR INTERMITTENTLY TRIGGERING A REFLEX-COORDINATED DEFECATION, which patent application in turn: (i) claims benefit of prior German Patent Application No. 10 2011 111 225.5, filed Aug. 20, 2011; (ii) claims benefit of prior German Patent Application No. 10 2011 118 943.6, filed Nov. 21, 2011; (iii) claims benefit of prior German Patent Application No. 10 2011 121 202.0, filed Dec. 16, 2011; (iv) claims benefit of prior German Patent Application No. 10 2012 005 607.9, filed Mar. 22, 2012; and (v) claims benefit of prior German Patent Application No. 10 2012 008 361.0, filed Apr. 25, 2012.

The seven (7) above-identified patent applications are hereby incorporated herein by reference.

FIELD OF THE INVENTION

The invention relates to a device for transanally introducing an infusion into the rectum or colon of a patient, said device comprising a catheter with a catheter shaft To ensure the most practicable and save catheter insertion possible, the catheter shaft is equipped in the proximal, preanal region with gripping depressions to accommodate the fingers gripping the catheter during insertion, securing that the catheter is inserted to an appropriate, atraumatic insertion depth.

BACKGROUND OF THE INVENTION

Catheters for transanally administering an infusion into the rectum or higher sections of the large bowel (colon) of a patient have been known in a wide variety of embodiments for many years.

Inflow catheters can be implemented as simple tube elements, but for improved retention of the catheter in the rectum they are also provided with an intrarectally placed balloon element. Such balloon elements provide, in addition to an anorectally anchoring function, a certain sealing effect that retains in the bowel the fluid that has been introduced by the irrigation. The sealing capacity of inflow catheters fitted with an exclusively intrarectal balloon component is inadequate in many cases, however, and must be created by the user by continuously manually repositioning the surfaces of the sealing balloon on the floor of the rectum or manipulating the position of the catheter shaft atop the balloon.

A major risk associated with the use of ordinary commercial catheters that are inserted transanally in the bowel continues to be perforation of the bowel wall due to improper handling, especially when inserting the catheter shaft too deep into the rectum and when exceeding the level of the rectum and prodruding with the catheter into the sigmoid section. Such perforations of the intestine have been preventable heretofore only by suitable education and sensitization of the user with respect to this particular set of problems.

The risk of an insertion associated bowel trauma is well known e.g. in patients with a spinal cord injury, not having the capability of physically sensing any manipulation done by an inserted catheter devive in the anus and the rectum. Paralyzed patients or patients suffering from forms of sensitive polyneuropathia can not determine the correct insertion depth of a trans-anally insertion catheter, when using conventional catheter designs.

Over the past ten years, a novel infusion technology that goes beyond the use of conventional transanal infusions has become established; in this new approach, the reflex-coordinated, active evacuation of the rectum and large portions of the left colon adjoining the rectum is triggered by intermittent, relatively small-volume, intrarectally introduced infusions. By consistent voiding of these segments of the intestine, the patient can thus be brought to a state of so-called "pseudo-continence" regardless of existing incontinence problems. The so-called transanal irrigation (TAI) method can be performed by the patient himself.

The function of the rectally instilled infusion medium, apart from some degree of mobilization of stool, is primarily to moderately expand the wall portions of the rectal ampulla (the terminal rectum), which then results in the triggering of the physiological stool evacuation reflex (reflex triggering). Whereas the rectally placed infusion medium usually causes such reflex triggering within a few minutes, it take can much longer, up to 30 minutes or more, for the administered irrigation volume to be fully voided from the rectum or colon. The relatively long time required for TAI limits its acceptance by many patients, and often rules this method out despite the fact that it is, as a rule, efficient for use by the individual.

Another problem is that many users are not able to manually bring irrigation catheters of conventional design into an adequately sealing position and keep them there.

Furthermore, as the balloon component of a conventional catheter is expanded inside the rectum, a reflex-triggering expansion of portions of the bowel wall can occur when the filling process has only just begun, thereby leading, inter alia, to a reflex-like opening of the anus and thus sometimes causing the anchoring balloon to slip out of the rectum.

Furthermore, commercially available devices for intermittent transanal irrigation, such as, for example, Peristeen Anal Irrigation, made by Coloplast, Denmark, are of relatively elaborate design, and are often only conditionally suitable for use outside the patient's familiar domestic surroundings.

To improve user acceptance of transanal irrigation, a catheter technique would be desirable which, once the catheter shaft is inserted in the rectum, holds it in its transanal position without the need for continuous repositioning, and both keeps the body of the shaft from sliding on into the bowel, with potentially traumatic consequences, and reliably prevents the catheter from accidentally slipping out of the anus prematurely.

Greater convenience in terms of the transanal placement of the catheter is offered in this regard by inflow catheters having a double balloon arrangement. Here, two separate balloon elements, which are usually filled simultaneously via a single filling lumen, are mounted in spaced relation on the catheter shaft. These come to lie on both sides of the anal canal, i.e. the internal and the external, thus mutually taking on the structures of the anus. When the wall of the balloon is expanded under pressure, the usually elastic implementation of the balloon material brings about a spherical enlargement of the balloon bodies and thus a certain axially exerted squeezing of the anus disposed between the balloon bodies. The dislocation-proof positioning of the catheter shaft obtained with such catheters can be assumed to be relatively reliable. A problem resides in the sometimes high filling pressures needed for the elastic expansion of the envelope, which are felt by patients as an uncomfortable or even painful foreign body sensation. Further, the elastic expansion of the intrarectal balloon to a tightly filled sphere can lead to direct triggering of the defecation reflex, which, in turn, in the presence of simultaneous rectal contraction and declining sphincter muscle tone, will in the most unfavorable case cause the catheter to slide out and the irrigation fluid to be voided prematurely.

DE 10 2004 033 425 B4 describes a sealing system for the management of rectal or anal incontinence having a particular embodiment for the tamponade of bleeding hemorrhoids, presenting a waisted balloon element having a terminal intrarectal or preanal section. The balloon envelope of the device is placed on the balloon-supporting shaft body in such a way that during the filling process, the intrarectal balloon segment moves in the direction of the rectal floor and there exerts a tamponade pressure on the bleeding venous blood vessels. The preanal balloon segment concurrently moves toward the external anal opening. The result is a tamponade effect oriented axially to the anus from both sides. In addition to the axial tamponade of the bleeding, the middle, waisted section of the balloon expands outward radially to the wall of the anal canal. It is preferably shaped with a diameter that exceeds the diameter of the opened anal canal. In the described device for the acute management of venous anorectal bleeding, in the in-use state the tip of the shaft body protrudes freely and unprotectedly into the intestinal lumen and poses a potential risk of injury.

WO 2007/118621 A1 describes a similar dumbbell- or hourglass-shaped balloon sealing system. The object there is to provide a seal against involuntary leakage of stool for intermittent periods of a few hours in chronically anorectally incontinent patients. This managing device also prominently features the rolling movement of the terminal balloon segments from both sides axially toward the anus. Here again, in the transanally placed state, the tip of the shaft body supporting the balloon protrudes freely and potentially traumatizingly into the intestinal lumen.

Both devices describe an hourglass- or dumbbell-shaped balloon configuration, the anus being received in the waisted region of the balloon, i.e. the region that is tapered relative to the terminal portions thereof. Such shaping of the balloon not only results in relatively good securing of the catheter against dislocation, due to the sealing of the balloon inside the anal canal on all sides, but also makes for a considerable improvement in sealing performance over that of conventional double balloons. In addition, both devices make it possible to largely avoid any expansion of the balloon envelope that could trigger irritation, pain or a defecation reflex, since the balloon wall is preferably already shaped to its working dimensions or beyond. Thus, the filling or unfolding of the balloon to its working state requires only a low filling pressure, equal to or only slightly greater than the pressure prevailing in the rectum or abdomen at the time.

Nevertheless, a particular disadvantage of the embodiments described in DE 10 2004 033 425 B4 and WO 2007/118621 A1 has proven to be that the distal tip of the shaft body supporting the balloon becomes freely exposed during the filling process and protrudes into the intestinal lumen, potentially causing irritation or injury to the bowel wall there during use.

SUMMARY OF THE INVENTION

The problem initiating the invention is to eliminate these disadvantages of the known prior art.

This problem is solved, in an arrangement of the cited species, by virtue of the fact that both balloon ends taper to the shaft dimension of the catheter shaft supporting the balloon and are fixed in a simply invaginated or inverted manner on the preferably outer jacket surface of the catheter shaft in such fashion that as the balloon is filled, the two radially enlarged balloon sections move toward each other in opposite axial directions, and wherein the two radially enlarged balloon sections are enlarged relative to the tapered, middle balloon section, such that when the balloon is placed transanally, during the filling process the two radially enlarged balloon sections draw down over the middle, tapered balloon section and in the limit case come into direct contact with each other, thereby limiting their relative movement and preventing the distal end of the catheter shaft from passing beyond the apex of the intrarectal balloon radius when the shaft body is in a position of maximum axial deflection.

To prevent, insofar as possible, lesions due to the tip of the shaft, the invention describes a specific, particularly advantageous ratio of the length of the middle, waist-like balloon segment to the invagination (inversions), on both sides, of the fixation points of the ends of the balloon shaft to the catheter shaft. This ratio ensures that in the filled, transanally positioned state, the tip of the catheter shaft spontaneously retracts into the intrarectal balloon segment and is nestled atraumatically there. The atraumatic securing of the catheter tip inside the intrarectal balloon segment is also ensured according to the invention when the shaft axis undergoes the deflections inside the anal canal that typically occur during use, of the kind readily caused by a tug or push on the tube connection through which the catheter is guided in.

The invention further addresses the problem of preventing undesired or premature triggering effects due to the filled balloon as it unfolds in the rectum. Triggering of the defecation reflex can be prevented in most cases by pre-shaping the balloon to the working dimension or beyond (residual dimensioning), since the filling pressures necessary for anchoring and sealing the catheter are largely the same as, or need be only a few millibars higher than, the pressures prevailing in the rectum or in the abdomen. The atraumatic securing of the tip of the catheter in the region of the intrarectal balloon segment is ensured even at such low filling pressures of, for example, 10 to 25 mbar.

Shaping the balloon to its working dimension further makes it possible for the user, by increasing the filling pressure or fill volume of the balloon from the initial filled state in which the balloon primarily has a sealing and anchoring effect, to induce a well-controllable and gradually increasable expansion of the bowel wall adjacent the catheter balloon, ultimately leading to controlled triggering of the defecation reflex with individually adjusted intensity.

In addition to the initial expansion of the wall of the rectum, a further suitable increase in the filling pressure in the dumbbell-shaped, waisted catheter balloon additionally causes a dilation of the anus or the anal sphincter, constituting another efficient trigger stimulus.

The intensity of such pneumatic expansion of the bowel wall or the anus can substantially exceed the intensity of reflex-triggering expansion with fluid media. Due to the more intense stimulus, several sequentially occurring cycles of evacuation reflexes can be triggered even though the stimulation is given only once.

This pneumatic expansion stimulus that can be well controlled by the user can also reduce the necessary amount of infusion fluid in many cases, which in turn can considerably shorten the time needed to evacuate the infusion from the rectum, thereby ultimately opening up the method to many users as a therapeutic option for self-administration.

The optional combined pneumatic/liquid triggering of reflexes described here eliminates the need for elaborate technical implementation of irrigation appliances, since in the preferred use case the necessary irrigation volume can be kept so small that it can be connected directly, as a compact, ready-to-use solution, via a fixed feed conduit to an inflow catheter designed according to the invention, and thus, in an ideal manner, be used as a disposable product.

For this purpose, the irrigation solution is preferably filled into a cylindrical, bag-like container, which the user can conveniently introduce intrarectally by squeezing it out with the hand.

The inflow catheter according to the invention further comprises a preferably fixedly glued-in filling conduit for charging the catheter balloon with filling pressure. The unit for filling the balloon is preferably implemented in reusable form, and can be configured as a hand-operated pump balloon connectable via a coupling, or alternatively a pumped balloon with a pressure-indicating manometer. Alternatively, volume-controlled filling of the balloon is also conceivable. Regardless of the filling arrangement, the user can determine by stepwise approximation the degree of filling of the balloon that is optimal for him, that which is best adapted to his individual anatomy and his current reflex status.

To ensure the most practicable catheter insertion possible and the reliable transanal placement of the tapered portion of the dumbbell-shaped balloon element, the catheter shaft is preferably equipped in the proximal, preanal region with gripping depressions to accommodate the fingers gripping the catheter during insertion. If the user has no sensitivity in the pelvic or anal region, he guides the catheter in with his fingers until they abut the anus, and can thus avoid uncontrolledly deep insertion.

BRIEF DESCRIPTION OF THE DRAWINGS

Further features, characteristics, advantages and effects of the invention will become apparent from the following description of preferred embodiments of the invention and by reference to the drawing. Wherein.

DETAILED DESCRIPTION OF THE PREFERRED EMBODIMENTS

Figure 1A:
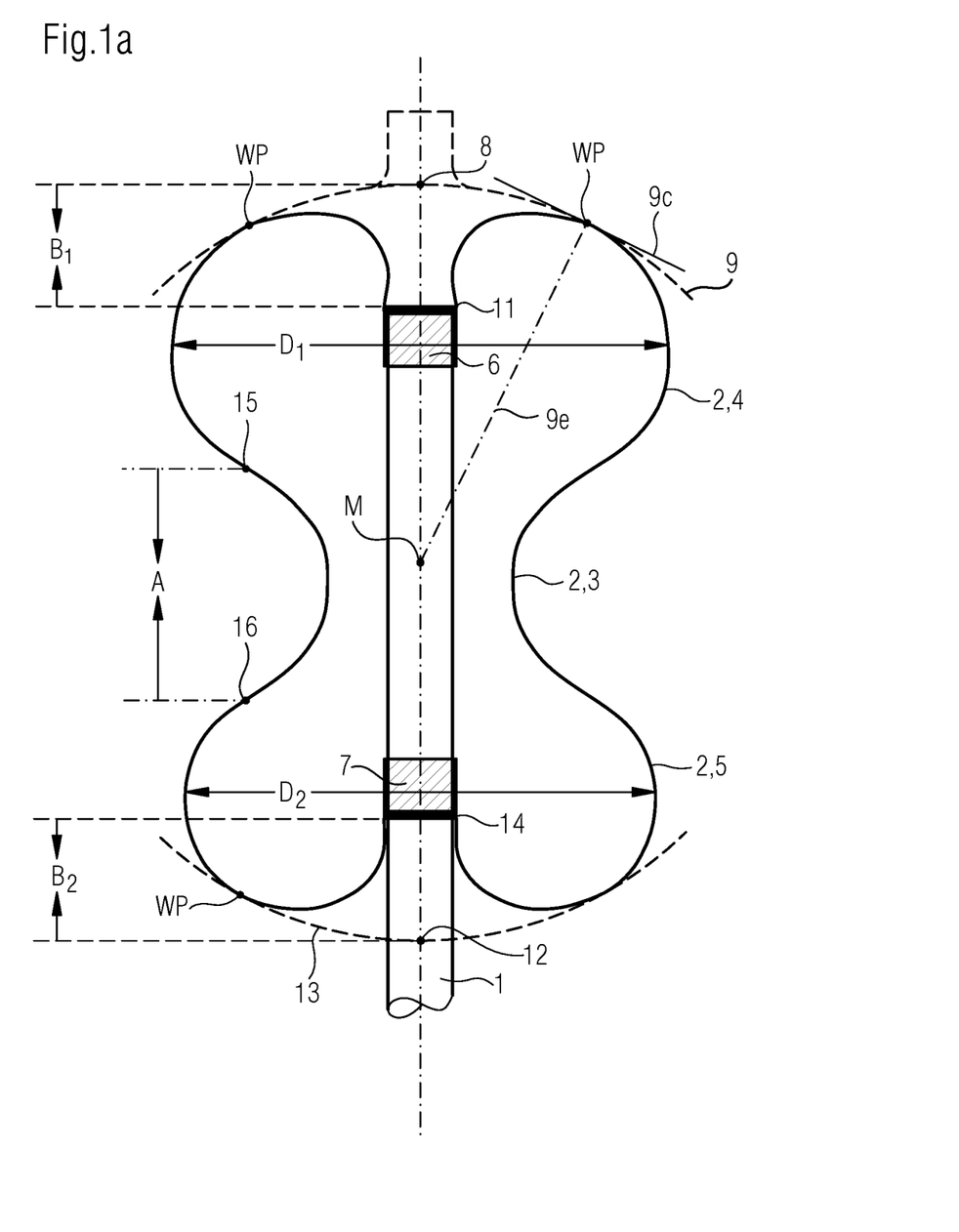
FIG. 1a shows an embodiment of a catheter according to the invention in a schematic longitudinal section, the balloon ends being mounted on the catheter shaft in an inverted manner according to the invention.

FIG. 1a shows a longitudinal section through an inflow catheter with a dumbbell- or hourglass-shaped balloon element 2 disposed at the distal end of the catheter shaft 1. The balloon element has, for example, a spherical or discoid expansion at each end. Disposed in the middle region between the terminal enlargements is a cylindrically or approximately cylindrically shaped segment 3 of reduced diameter, which continuously connects the intrarectal enlargement 4 to the preanal enlargement 5.

The balloon 2 terminally comprises two balloon shaft ends (6, 7) for attaching the balloon to the shaft. During the mounting of the balloon, the shaft ends 6 and 7 are invaginated (inverted) into the inside of the balloon by a defined magnitude B and in this position, in which they are displaced toward each other, are fixed on the shaft 1, for example by gluing or welding.

The sum of the magnitudes B of the inversions at both ends should be at least equal to the length of the tapered intermediate piece A (A smaller than/equal to the sum of the magnitudes B).

The inversion depth B at the end of the balloon facing the patient or the rectum corresponds to the distance from the apex 8 of the distal, intrarectal balloon radius 9 to the distal fixation line 11 of the balloon end 6 on the catheter shaft.

Figure 1B:
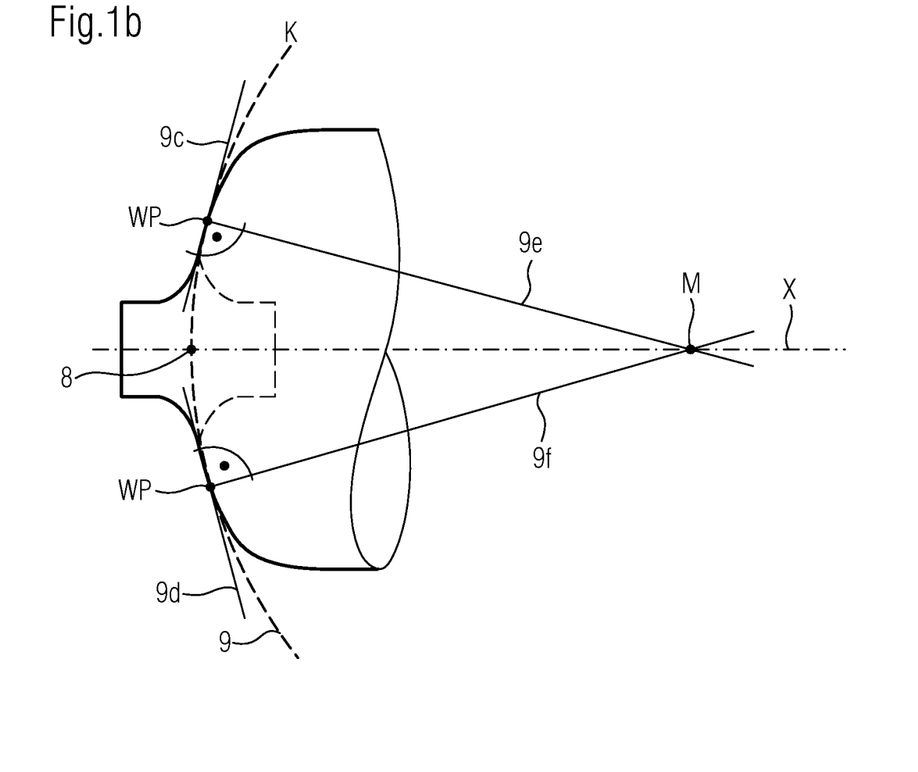
FIG. 1b shows the geometric structure of the apex of the distal balloon radius.

The distal radius 9 corresponds to the frontal radius during free, non-inverted unfolding of the completely filled but not pressurized balloon (broken line). An exemplary rule for geometrically determining the apex 8 to good approximation is illustrated in FIG. 1b. In particular, the drawing shows the two inflection points WP of the longitudinal section through the distal balloon end, which, by the inversion of the distal region of the balloon, result in the spherical or discoid or approximately semitoroidal region of the intrarectal section of the balloon. The normals 9e, 9f to the tangent to the longitudinal section of the balloon intersect with the longitudinal axis X of the catheter shaft at point M, and a circle K around this point M at the distance M-WP yields the forward apex 8, which marks the distal limit for the catheter shaft in its neutral, non-deflected initial position.

Figure 1C:
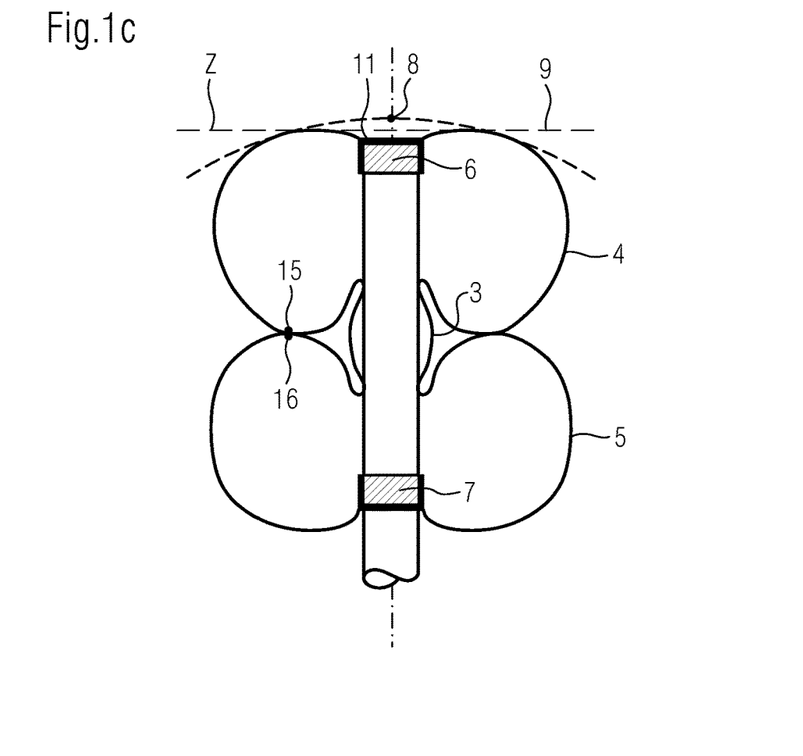
FIG. 1c shows the balloon body described in FIG. 1a in a freely unfolded state under low filling pressure, outside the anus.
Figure 1D:
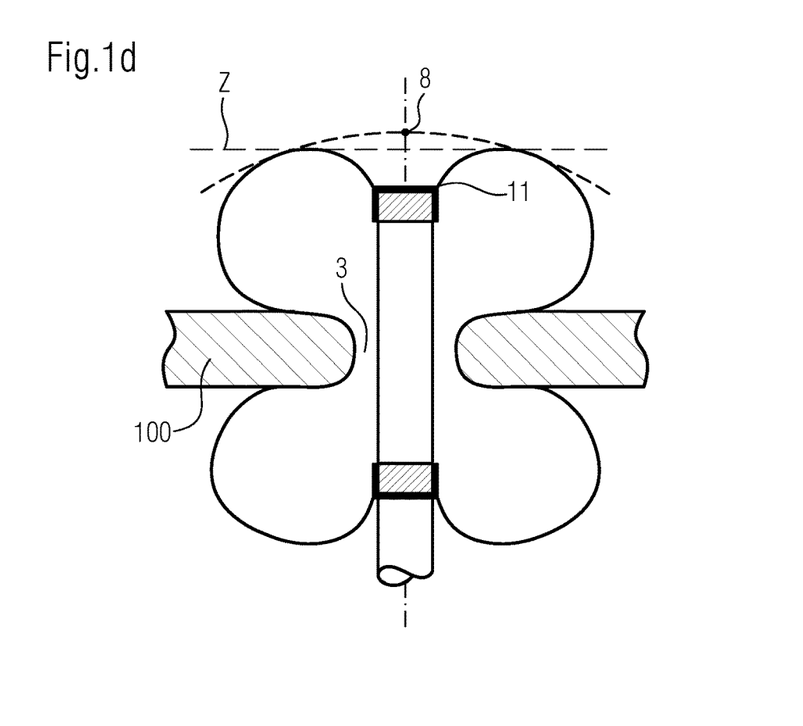
FIG. 1d shows the balloon body described in FIG. 1a in a transanally placed state, under filling pressure.
Figure 1E:
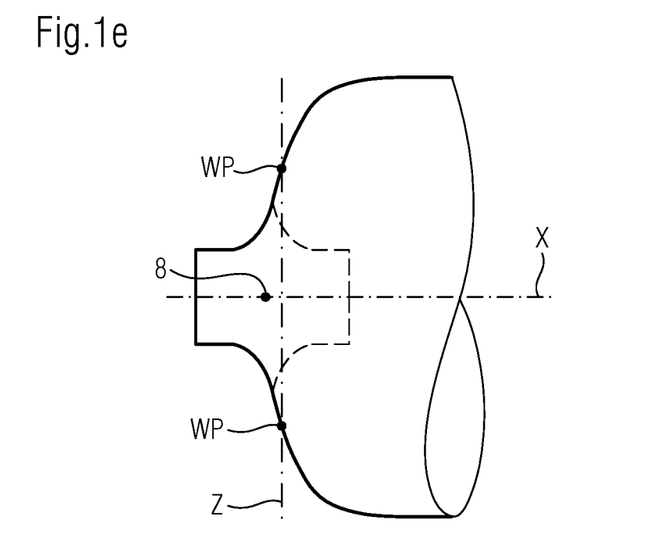
FIG. 1e shows the geometric structure of the distal plane tangent to the intrarectal balloon section.

It can be seen in FIG. 1e that a straight line can also be passed through points WP; this straight line represents the plane Z which after invagination of the forward end of the balloon is now tangent distally to the intrarectal portion of the balloon, and can also be taken as a measure of the distalmost position of the catheter shaft in its neutral, non-deflected initial position.

On the side of the balloon facing away from the patient, the inversion depth B corresponds to the distance from the apex 12 of the proximal, preanal balloon radius 13 to the proximal fixation line 14 of the balloon end 7 on the catheter shaft.

Radius 13 corresponds to the proximal radius when the balloon is freely unfolded without inversion. The geometric determination of apex 12 is similar to the approximation described in FIG. 1b.

The length of intermediate piece A is determined by determining the distance between the transitions of the shoulder radii 15 and 16 (inflection points) of the mutually facing shoulder surfaces of balloon segments 4 and 5.

The inversion depths, lengths and distances are each determined in the filled state under filling pressure, the filling pressure being so selected that the balloon unfolds completely but there is no elastic expansion of the balloon envelope.

The inversion depth B is calculated as follows: $B \geq A/2$ ($\geq$=represents greater/equal).

In mounting the balloon on the catheter shaft, the respective points for the inversion of each of the balloon shaft ends are the apex 8 of the distal, intrarectal balloon radius 9 and the apex 12 of the proximal, preanal balloon radius 13.

In the embodiment described in this figure, the distal fixation line 11 also corresponds to the distal end of the catheter shaft 1. The shaft terminates directly at the fixation line 11 and does not extend distally past this fixation line in the manner illustrated in FIG. 2.

FIG. 1b describes the geometric derivation of the apex of the distal balloon radius.

The forward balloon radius 9, frontally facing the intestinal lumen, of the intrarectal balloon segment 4 is illustrated as a broken line. It is constructed from the two inflection points 9a and 9b and the two inflection tangents 9c and 9d respectively belonging to these inflection points.

One of the two inflection points 9a or 9b is used to construct a straight line 9e or 9f that is normal to the respective inflection tangent 9c or 9d and intersects the corresponding inflection point 9a or 9b. The point of intersection of these straight lines 9e or 9f with the axis X of symmetry yields the center point of the circle K.

The circle K, and thus the forward balloon radius 9, results from the center point M of the circle and the inflection points 9a and 9b, which are on the circumference of the circle. In this derivation, apex 8 is obtained from the point of intersection of the circumference of the circle with the axis X of symmetry of the balloon.

For the description of the frontal apex 8 used below, the derivation of the farthest distally ranging point of the filled, unpressurized balloon envelope is performed, for purposes of simplification, using the point of intersection of the connecting line Z between the two inflection points 9a and 9b with the axis X of symmetry.

FIG. 1c shows the behavior of the catheter balloon that was inverted according to the invention in FIG. 1a as it unfolds freely and without pressurization, in the free, non-transanally placed state. The figure illustrates the counter-rolling movement of the two terminal balloon segments 4 and 5 made by possible by the specific inversion of the balloon ends 6 and 7 on the catheter shaft.

In a preferred, particularly thin-walled and soft-film-like implementation of the balloon body, the two segments move toward each other in response to the slightest, nearly ambient filling pressure and roll over the middle segment 3. When the two segments are in contact in the region of the transition points (15, 16) of the shoulder radii, the apex 8 of the radius 9 is flush or nearly flush with the distal fixation line 11 of the distal balloon shaft end 6 on the catheter shaft.

A configuration of this kind would correspond in situ to a clinical use situation in which the anal canal was maximally shortened in length. Even in this extreme case, it would thus be ensured by virtue of the described inversion rule that the free distal catheter shaft end, which here corresponds to the distal fixation line 11, does not extend into the intestinal lumen and even in the event of maximal lateral deflection of the catheter shaft in the rectum (tilting of the intrarectal portion of the shaft toward the bowel wall) does not come into contact with the wall of the intestine and pass beyond the distal balloon radius 9, as a maximum limit precluding irritation and lesions of the bowel wall.

FIG. 1d shows how the inversion of the balloon ends in relation to the distal catheter shaft ends described in FIG. 1a presents itself in cases where the anal canal is of normal or only slightly shortened length. In this more common clinical use situation, the forward fixation line 11, which here corresponds in turn to the distal free end of the catheter shaft, is shown to be deflected substantially into the interior of the intrarectal balloon 4. As the balloon is charged with pressure, the two terminal balloon segments 4 and 5 move counter to each other toward the anus and so conform to the particular anal situs. Given a suitably thin-walled implementation and soft-film-like character of the balloon envelope, the counter-rolling of the balloon segments commences even in response to a very low pressure force (filling pressure) that gives an impression of being nearly ambient to the environment.

The mere individual intra-abdominal pressure bearing against the transanally placed balloon or acting on the balloon is sufficient to produce a combined transanal sealing effect, comprised of radial sealing with respect to the anal canal and axially oriented sealing brought about by the counter-rolling movement of the terminal balloon enlargements at the inner and outer outlets of the anus. The sealing effect thus is not contingent on the balloon initially being filled beyond its volume and unfolding freely until the balloon envelope begins to expand. The balloon can behave in the described axial counter-rolling and radial unfolding fashion, even under partial filling of, for example, 70 to 90% of its volume when freely unfolded on the catheter shaft. This enables the balloon catheter to be placed in the anus in a nearly pressure-neutral and irritation-free manner.

In the presence of normal or slightly modified anal anatomy, any traumatizing effect of the tip of the catheter shaft on the bowel wall can thus be precluded, even under completely pressure-neutral charging with a filling medium, by the inversion of the shaft tip that occurs according to the invention.

Figure 2:
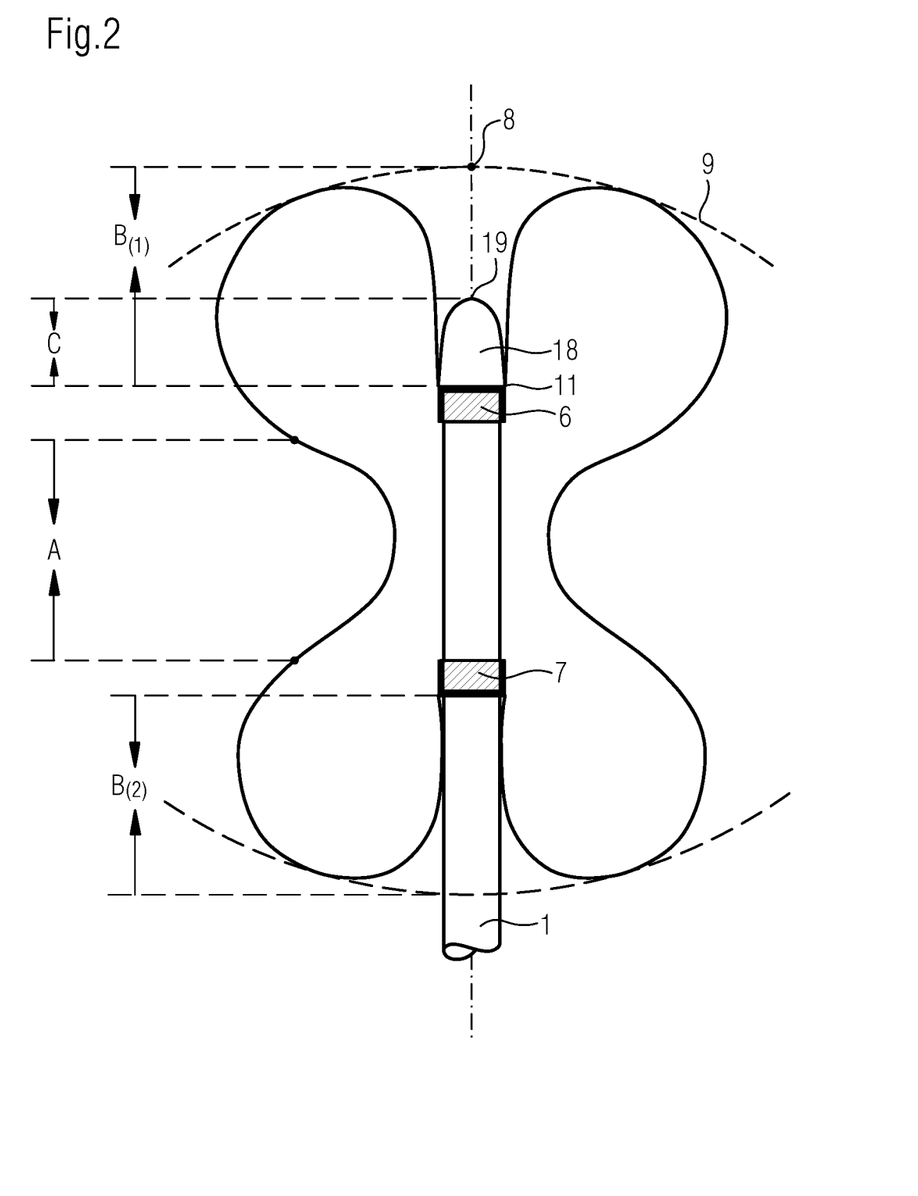
FIG. 2 is a representation similar to FIG. 1a of another embodiment of the invention, in which a catheter tip extends beyond the forward fixation line of the end of the balloon shaft.

FIG. 2 shows, by way of example, how sections of the catheter shaft in the form of a tip piece 18 that extend beyond the distal fixation line 11 in a distal prolongation directed toward the bowel are to be considered in determining the inversion depth of the balloon ends 6 and 7, in order to ensure atraumatic inversion, according to the invention, of the distal end of the catheter in the intrarectal balloon during transanal placement of the filled catheter balloon. The length C of the tip piece 18 is defined as the distance from the forward fixation line 11 to the forward apex 19 of the tip piece.

Length B is increased in comparison to FIG. 1a by the magnitude of length C or C/2.

The corresponding inversion depth B is preferably calculated taking into account a tip piece in the form: B>=A/2+C.

Alternatively hereto, the corresponding inversion depth B can, less preferably, be obtained considering a tip piece according to the relation: B>=A/2+C/2.

Figure 3:
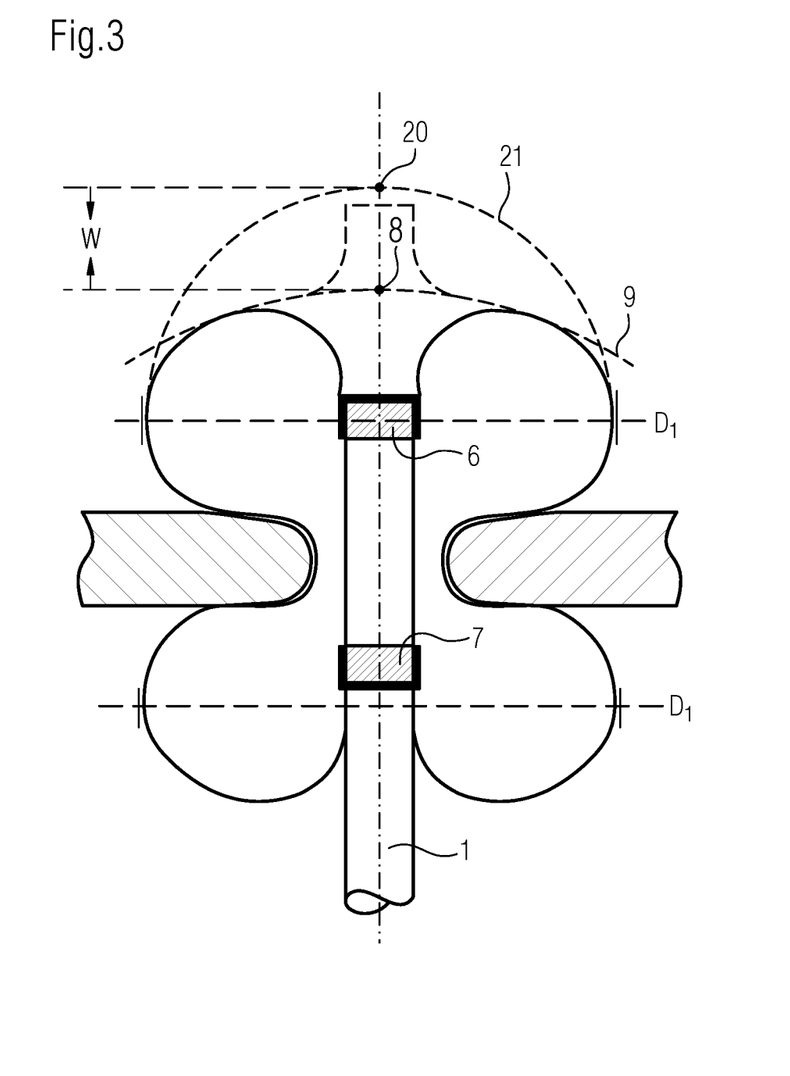
FIG. 3 is a representation similar to FIG. 2 showing additional auxiliary lines, such that the reference point for determining the inversion depth B is not the forward balloon radius, but rather the largest diameter D of the intrarectal balloon segment.

FIG. 3 illustrates another, alternative rule for establishing the inversion depth B of the balloon shaft ends 6 and 7 on the catheter shaft 1 in relation to the distal catheter shaft end 11, 19.

This rule particularly considers a possible axially oriented deflection of the catheter shaft inside the filled, transanally placed balloon. In the context of the inventively described inversion of the balloon shaft ends on the catheter shaft supporting the balloon, such deflection of the shaft in the longitudinal axis could cause the distal end of the catheter shaft to be deflected toward the bowel, thus creating a potential risk of perforation.

The maximum distal deflection W of the forward fixation line 11 is defined as a distance that emanates from the apex 8 of the radius 9, forming a distally directed prolongation of the longitudinal axis of the shaft, and extends to the apex 20 of a radius 21, said radius 21 being constructed over the largest diameter D of the intrarectal balloon segment 4.

If the catheter shaft has a tip piece 18 that extends beyond line 11, the maximum deflection path W should be correspondingly selected so that upon maximum deflection W of the shaft, the tip 19 of the tip piece does not extend past radius 21.

The radius 21 defined by the largest diameter D in the intrarectal balloon segment constitutes a fundamentally relevant boundary line for distal portions of the catheter shaft. In the event of lateral tilting of the shaft longitudinal axis of the transanally placed catheter shaft, the fact that the maximum deflection W is referred to the largest balloon diameter D ensures that the catheter shaft tip (11, 19) still moves within the pivot radius 21 of balloon segment 4, thus preventing relatively well any potential traumatizing contact of the tip with the bowel wall adjacent the balloon.

In determining the inversion depth B, the particular ratio of the distance W to the radius 21 or of the diameter D on which it is based is preserved and the inversion depth B is adjusted accordingly as necessary.

Figure 4:
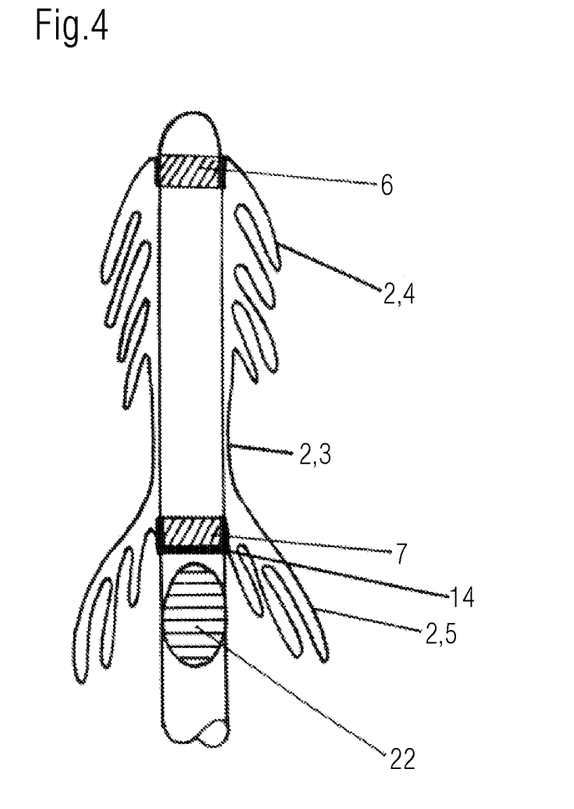
FIG. 4 shows a shaped balloon envelope in the unfilled state, provided in a particularly advantageous manner for rectal insertion and reliable transanal placement and unfolding of the balloon, as well as specially molded gripping areas for the determination of an appropriate, atraumatic insertion depth.

FIG. 4 shows the catheter balloon 2 in its emptied form, in which it lies against the catheter shaft ready for insertion in the anus. The envelope segments of the intrarectal balloon 4 and of the middle segment 3 cling to the shaft in folds.

In this state, the two envelope portions preferably come to lie approximately at the height of the line segment between the fixation points of the balloon ends 6 and 7 on the surface of the shaft. The envelope of the preanal balloon segment 5, by contrast, is preferably smoothed out in the proximal direction and protrudes past the fingers gripping the catheter for insertion, the preferred gripping point being located just proximal of the proximal fixation line 14. The gripping point 22 is preferably implemented as a depression-like receiving surface, one such preferably being provided on each of the opposite, 180°-apart shaft surfaces.

The evacuated balloon being fixed in such fashion, the user grips with his fingers under the envelope of segment 5, which envelope is smoothed out in a proximal direction, and guides the catheter into the rectum until the gripping fingers abut the external anus. A defined insertion depth of the distal catheter portion is thereby ensured. It is further ensured that the intrarectal balloon section 4 is inserted into the rectal cavity, while the proximal balloon portion 5 comes to lie outside the anus (preanally). Reliable transanal positioning of the catheter therefore occurs as the waisted balloon is filled.

Keeping the catheter at the gripping point 22, when inserting the catheter, a paralyzed patient or a patient with a loss of sensitivity in the perianal or pelvic area, senses the moment the fingertips touch the anal rim, indicating that the correct insertion depth of the catheter tip has been reached.

Figure 5:
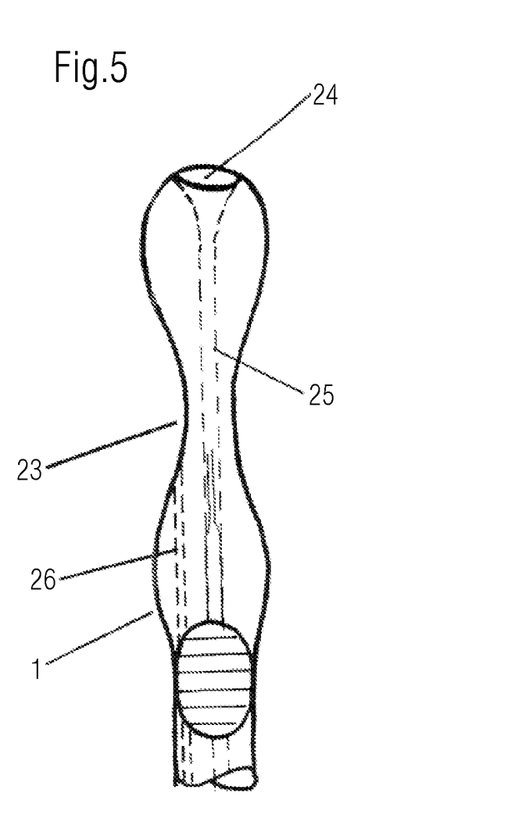
FIG. 5 shows a modified embodiment of the invention illustrating a catheter shaft, wherein the cathether shaft is waisted in its transanal section and comprises adjacent gripping areas, where the balloon is not shown in this Figure to allow a clear view onto the catheter shaft; in the completed product, the balloon has to be fixed to the catheter shaft shown in FIG. 5 in a similar manner as shown in FIG. 4.

FIG. 5 shows a preferred implementation of the shaft body 1 that furnishes some degree of automatic positioning and securing of the shaft in the anus even when the catheter balloon has not yet been filled. The shaft 1 has for this purpose a likewise waisted shape, which is correspondingly tapered in the transanal region 23 and in effect locks the catheter shaft in a transanal position in this region after insertion. The catheter shaft preferably also has a distally terminal, funnel-like, atraumatically shaped opening 24 that connects to the duct 25 supplying the medium.

The figure also shows the particular spacial correspondency of the waisted shaft section 23 and the gripping point 22. Having inserted the catheter to the point where the gripping fingers touch the anal rim, the waisted section is positioned transanally, taking up the anal sphincter, and depending on the sphincter tone, snapping into transanal position. The patient can then release the fingers from the catheter shaft, while the appropriate position of the catheter is secured by the waisted transanal shaft region.

In a particularly large-volume implementation of the intrarectal balloon segment or a longitudinal expansion of the balloon segment that reaches far into the rectum, the balloon segment, in the non-air-filled, ready-to-use state, can optionally be stuffed or packed partially into the opening 24. It then slips out of the opening as the inserted catheter is filled.

Given suitable implementation of the shaft material, the waist 23 can also predefine a certain kinkability of the shaft body, thus improving its atraumatic properties.

The filling of the balloon takes place through a separate duct 26 integral to the shaft.

To prevent backflow of irrigation fluid, the inflow catheter can be equipped with a non-return valve in the region of the fluid-conveying duct 25.

The valve can preferably consist of a thin-walled tube element having a wall thickness of few, preferably, 5 to 15 micrometers and the diameter of the duct 25, the distal end of the tube lying freely in the duct 25 over a length of approximately 5 to 10 mm and its proximal end being connected sealingly to the inner wall of the duct 25. As the medium flows through the duct in the direction of the tip, the tube element opens and allows the medium to flow freely. In response to flow in the reverse direction, the tube element collapses and closes up sealingly, preventing an effective backflow.

Figures 6, 7:
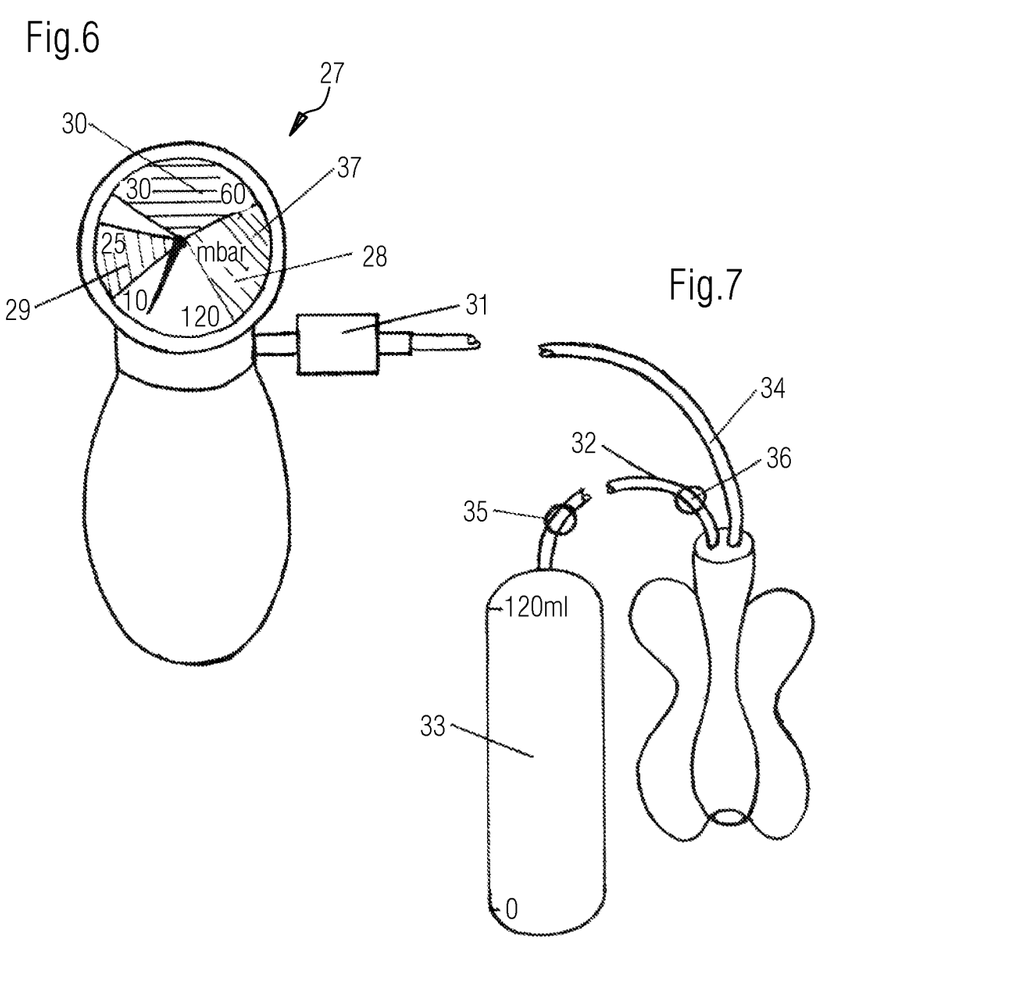
FIG. 6 shows a manually operable pump manometer with a pressure scale equipped for multi-stage, sequential filling of the catheter balloon.
FIG. 7 shows a further modified embodiment of the invention with an infusion container fixedly connected to the catheter shaft and a filling tube for charging the catheter balloon with filling pressure.

FIG. 6 schematically illustrates a pump manometer 27 equipped with a scale 28 suitable for the filling of the inventive catheter balloon in multiple steps or with a sequential increase in filling pressure. The scale preferably displays, on the one hand, an initial, low pressure range 29 (app. 10-25 mbar), which is set by the user after inserting the catheter and before introducing the infusion fluid, and which, given the inventive preshaping of the balloon envelope and its fixation on the shaft, is sufficient in most cases to ensure transanal anchoring and sealing of the catheter without a direct reflex-triggering effect on the bowel wall.

When the user then initiates an increase in the filling pressure in the balloon into range 30 (30-60 mbar, with increasing corresponding expansion of the rectal portions of the bowel wall) or into range 37 (60-120 mbar, with increasing additional expansion of the anal sphincter), the user is ultimately able to generate a trigger stimulus of largely reproducible intensity in order to trigger a defecation reflex. The user thus has the advantage of being able to avoid an evacuation reflex in the presence of an initially low balloon pressure merely having an anchoring and sealing action, and thus of being able to retain the infusion fluid in the bowel long enough for his individual needs, resulting in better dissolution or suspension of stool in the fluid. On the other hand, by intentionally causing an increase in pressure in the balloon, he can generate an intense, relatively prompt-acting reflex-triggering stimulus, which can, if necessary, exceed in intensity the triggering effect of a column of colorectal fluid.

The catheter balloon is preferably filled with air, through a fill line integrated into the shaft wall of the catheter body 1.

In addition to pressure-controlled filling of the balloon using a pump manometer, as illustrated in FIG. 6, volume-controlled filling can be achieved with the use of an additional syringe element that specifies the preferred fill volume by means of a suitable marking on the syringe body. The filling of the balloon is preferably partial, in the form of one-step filling. In the ideal case, therefore, in loose, unexpanded form, the balloon lies against the structures of the bowel and the anus. The balloon envelope thus absorbs the forces acting on the balloon in the rectum, the anus and the preanal region and brings the balloon into the configuration in which it performs the anchoring and sealing function. The respective physiologically acting forces are absorbed by the catheter balloon and thus enable the balloon to be placed anorectally in as pressure-neutral a manner as possible, largely precluding undesired and premature triggering effects.

A volume-controlled filling of the balloon can also be a two-step process, in which incomplete filling is first performed and the balloon is then, in the second filling step, filled with a volume that has a triggering effect. The pressures developed in the transanal balloon in response to the particular volume should preferably fall within the pressure ranges (29, 30) described in FIG. 6, and are to be determined by and for the user on an individual basis, as in the case of pressure-controlled filling.

To limit the filling pressure or prevent critically high balloon filling pressures, in the case of both manometer- and syringe-actuated filling a pressure limiting valve 31 can be interposed between the filling element and the catheter, to prevent, for example, balloon filling pressures over 120 mbar.

FIG. 7 shows a preferred embodiment of an inflow catheter, which transitions at the proximal end to two feed conduits that are preferably fixedly connected to the shaft, feed conduit 32 being fixedly connected to a preferably bag-like container 33 containing infusion medium, and thus constituting a ready-to-use unit comprised of catheter and medium.

The volume of the container 33 must be dimensioned in this case to accommodate approximately 80 to 120 ml of irrigation solution. The relatively small quantity is squeezed out manually by the user and thus introduced into the rectum by repeated squeezing. To make it possible to grip the container even with impaired hand motor function, the container is preferably shaped as cylindrical, with a diameter of approximately 4-6 cm.

Figure 7A:
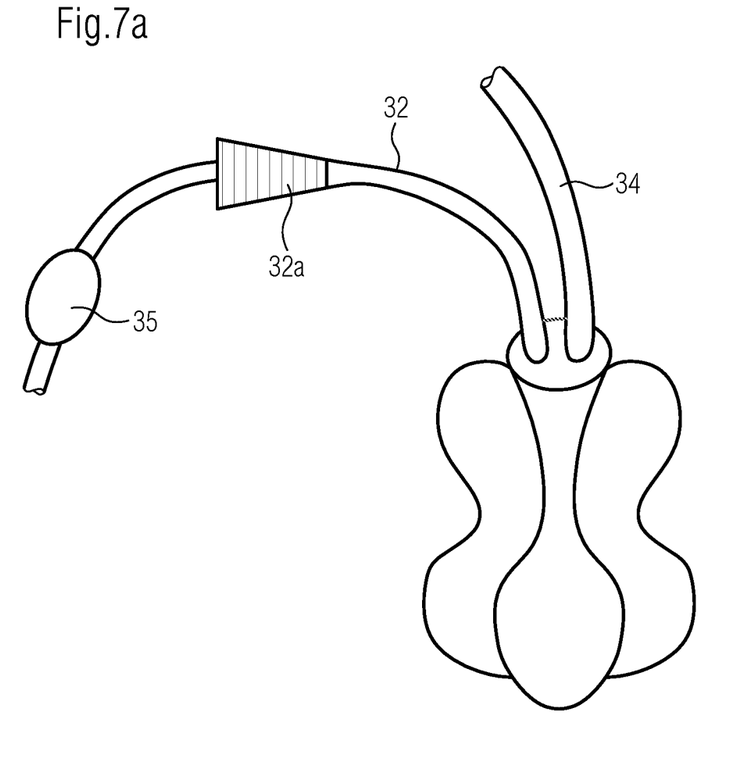
FIG. 7a shows another modified embodiment of the invention where an infusion container is releasably connected to the catheter shaft and can be replaced by another equipment.

Furthermore, as can be seen in FIG. 7a, connection can preferably be equipped with a seal 35 that can be broken by bending and that releases the irrigation solution. It is also advantageous to provide a non-return valve 36, which is integrated into the fluid-conveying arm of the ready-to-use device and which permits the directed emptying of the container without backflow. The connection optionally ends proximally with a funnel like connector 32a, allowing for a multi-fit connection to a variety of off-shelf, ready to use irrigation solutions.

Another feed conduit 34 can be connected directly to a pump manometer 27 or a filling syringe.

Figure 8:
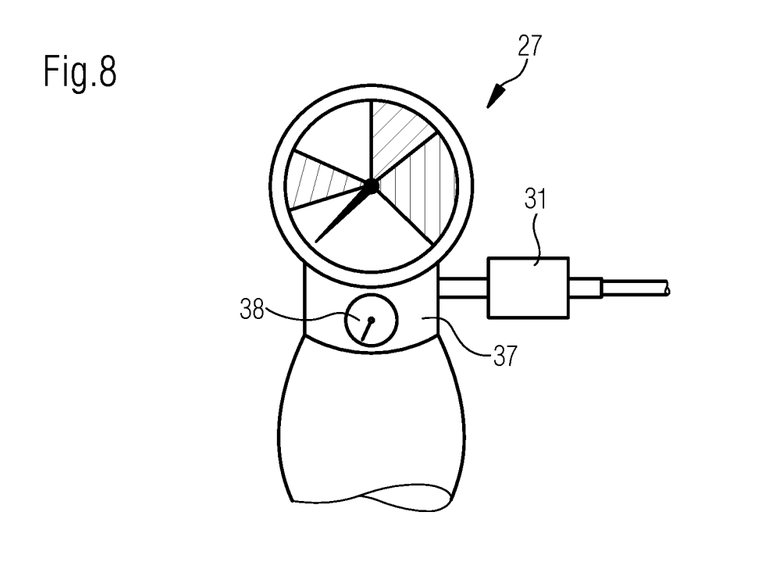
FIG. 8 shows a pressure decompressing module 37, that once the reflex is released and the bowel begins to contract, fully opens and decompresses the catheter balloon to environment.

FIG. 8 shows a pressure decompressing module 37, that can be operated as a stand-alone device, or modularly integrated into a pump manometer as pictured in FIG. 6. The module works by e.g. a spring operated opening mechanism, which continuously opens the filling line 34 and the balloon to the ambient environment, fully decompressing the balloon. The threshold for opening the mechanism can be set by user individually to a certain balloon pressure, by an adjustable trigger knob 38. As pictured, the module can be positioned in between the scale and the pump balloon of the manometer. The pressure decompressing module is of particular benefit for e.g. spinal cord injury patients, not being able to sense stool urge or the onset of peristaltic bowel contraction. Once the reflex is released and the bowel begins to contract, the catheter "opens" and can be pulled out or expelled from the rectum.

The balloon is made from polyurethane material, or from a material with a similar compliance and elasticity characteristics. Preferably, when using polyurethanes, the balloon has a Shore A durometer of 80 to 95, preferably of 80 to 85.

The wall thickness in the enlarged distal terminal balloon section being adapted to be placed intrarectally is 3 to 6 times thinner than the wall thickness in the tapered balloon section being adapted to be placed transanally, especially 4 to 5 times thinner.

The wall thickness in the enlarged distal terminal balloon section being adapted to be placed intrarectally is 10 to 30 μm, especially 15 to 25 μm.

The thickness of the wall in the tapered balloon section being adapted to be placed transanally is 30 to 180 μm, especially 60 to 125 μm.

The use of only slightly volume-expandable (compliant) materials, such as, for example, polyurethane (PUR), for example of the specification Pellethane 2363 80A to 90A, Lubrizol Corp., is preferred, since these materials have good dimensional stability in the lowest wall thickness range, including as balloon films, in the pressure range of approximately 10 to 120 mbar.

Such thin-walled PUR balloon films formed into complex shape can preferably be produced by hot molding from previously extruded raw tubing material, which, with suitable stretching of the tube blank before tempering, permits a polymer orientation and lends the shaped balloon films exceptional mechanical strength.

It is also conceivable to use polyurethanes of low Shore hardness, for example in the range of 60 to 75A, to impart a volume-expandable behavior, with a relative loss of dimensional stability, to the catheter balloon in the wall thickness range of less than 40 µm, and preferably less than 15 µm, in the typical filling pressure range during use of 10 to 120 µm.

Alternatively, non-volume-expandable, non-elastic materials can be used, such as polyethylene, PVC or mixtures of the aforesaid materials with polyurethane.

Balloon films according to the invention can also be shaped directly from the extruded, still soft, largely amorphous tube molding compound (in-line molding), in which case the achievable strengths of the films are much lower than those of pre-extruded tubes and the attainable wall thicknesses are much higher than in the case of forming from pre-extruded material.

Dipping processes using liquid PVC or PUR materials can also be contemplated for production.

The welding together of single layers of film to form balloon bodies is also conceivable.

The connection of the balloon to the shaft body is effected by gluing, by thermal methods, or alternatively by shrinking the balloon ends onto the shaft body.

In the freely unfolded, unpressurized state, the balloon segments, in the unpressurized state, should have diameters and length dimensions of:
 intrarectal: 40-80 mm, preferably 50 to 70 mm, measuring a length of 30 to 60 mm, preferably 35 to 45 mm;
 transanal: 10 to 35 mm, preferably 20 to 25 mm, measuring a length of 20 to 50 mm, preferably 25 to 35 mm;

In addition to the transanal use of the inflow catheter, the embodiments according to the invention can also be used for perforation-safe placement of a transanally inserted drainage tube for, among other purposes, the ongoing drainage of stool from a patient's intestine. Further, the described catheter technique may also be contemplated for use in surgically created stomata/openings or other natural body openings.

The invention claimed is:

1. A device for transanally introducing an infusion into the rectum or colon of a patient, said device comprising a catheter with a catheter shaft and an inflatable balloon mounted to the catheter shaft, wherein, in order to ensure safe catheter insertion so as to avoid an inadvertent perforation of the bowel wall due to an improper handling upon insertion of the catheter into the rectum or colon of the patient, the catheter shaft is equipped in the proximal, preanal region with at least one gripping depression (22) recessed into an outer surface of the catheter shaft, whereby to accommodate at least one finger of the patient during insertion of the catheter into the rectum or colon of the patient, wherein a distance between the catheter tip and the at least one gripping depression is equivalent to a correct and safe insertion depth of the catheter in the rectum or colon of the patient, such that the gripping depressions of the catheter, upon guiding the catheter in with the patient's at least one finger disposed on the at least one gripping depression, are able to restrict the movement of the catheter when the at least one finger of the patient is disposed on the at least one gripping depression (22) abut the anus, facilitating catheter insertion by a patient lacking sensitivity in the pelvic or anal region, whereby to avoid uncontrollably deep insertion of the catheter.

2. The device according to claim 1, wherein the catheter shaft has a waist (23) in the region of its transanal placement inside the anal canal.

3. The device according to claim 2, wherein the waist (23) is positioned in a suited, distal distance from the at least one gripping depression (22), ensuring that when the catheter is inserted to the level of the at least one gripping depression (22), the catheter waist (23) is snugly positioned inside the anal canal.

4. The device according to claim 1, wherein the inflatable balloon comprises a distal terminal balloon section of larger radius and generally spherical or discoid shape, and, disposed proximal to this distal terminal balloon section, a tapered balloon section having a reduced radius, the tapered balloon section of the device being adapted to be placed transanally, such that the enlarged distal terminal balloon section is placed intrarectally, wherein the balloon is mounted to the catheter shaft only at fixation points located at the ends of the balloon, wherein both balloon ends taper approximately to a shaft dimension of the catheter shaft supporting the balloon.

5. The device according to claim 4, wherein the catheter balloon, or the tapered balloon section, terminates flush with the anus.

6. The device according to claim 5, wherein the at least one gripping depression (22) of the catheter shaft are disposed proximally adjacent the end of the catheter balloon, especially with the end of the catheter balloon terminating flush with the anus.

7. The device according to claim 4, wherein the tapered, transanal balloon section is extended into a preanal balloon section.

8. The device according to claim 7, wherein the enlarged distal terminal balloon section adapted to be placed intrarectally and the tapered balloon section adapted to be placed transanally are manufactured separately, and/or are mounted from different materials or with different compliance and elasticity characteristics.

9. The device according to claim 8, wherein the tapered balloon section adapted to be placed transanally has less volume-expandable characteristics and/or less elasticity than the enlarged distal terminal balloon section adapted to be placed intrarectally.

10. The device according to claim 4, wherein the inflatable balloon has a waisted shape, comprising the distal terminal balloon section of larger radius and generally spherical or discoid shape, a proximal terminal balloon section of larger radius and generally spherical or discoid shape, and, disposed between them, the tapered balloon section having a reduced radius, wherein the tapered balloon section of the device is adapted to be placed transanally, such that the enlarged distal terminal balloon section is placed intrarectally and a proximally adjoining radially enlarged balloon section is placed extracorporeally, or preanally.

11. The device according to claim 10, wherein the proximal, radially enlarged balloon section adapted to be placed extracorporeally or preanal extends, in the uninflated state of the balloon, in a pocket-like manner over the at least one gripping depression.

12. The device according to claim 4, wherein the at least one gripping depression is disposed on the shaft in direct proximal adjacency to a proximal balloon fixation line.

13. The device according to claim 4, wherein the ends of the inflatable balloon, beginning at an inflection point of their longitudinal section, are inwardly invaginated, or inverted, and in the inverted or invaginated state are fixed on an outer surface of the catheter shaft.

14. The device according to claim 4, wherein the ends of the inflatable balloon are fixed on an outer surface of the catheter shaft such that, at a transanally placement of the balloon in situ, the balloon waist seals inside and against the anal canal in a radial direction on all sides.

15. The device according to claim 14, wherein, at a transanally placement of the balloon in situ, an axis of the catheter shaft can be displaced inside the anal canal by a tug or push on a tube connection through which the catheter is guided in.

16. The device according to claim 15, wherein, as the balloon is filled, the two radially enlarged balloon sections move toward each other in opposite axial directions, whereby to be drawn over the middle tapered balloon section.

17. The device according to claim 16, wherein, as the balloon is filled, the distal tip of the catheter shaft, in its non-displaced resting state, retracts into a protected, injury-preventing position inside the intrarectal balloon section and, in so doing, comes to lie entirely proximally of a distal apex of a circle about a center point which is located on an axis of symmetry and whose tangent in an inflection point corresponds to a tangent to the non-invaginated longitudinal section of the balloon.

18. The device according to claim 17, characterized in that the distal tip of the catheter shaft in its non-deflected, resting state comes to lie entirely proximally of a plane (Z) which is intersected perpendicularly by the axis (X) of symmetry and which is fully tangent distally to the intrarectal balloon section.

19. The device according to claim 17, characterized in that the middle, tapered balloon section is separated from each of the approximately spherical or discoid balloon sections by a respective inflection point of the cross-sectional radius and in the non-expanded filled state has an axial length (A) that is preferably larger than its minimum diameter.

20. The device according to claim 17, characterized in that in the non-expanded filled state, the invaginated or inverted balloon ends each have an axial extent ($B_1$, $B_2$) that is preferably greater than their minimum diameter.

21. The device according to claim 4, characterized in that in a non-expanded filled state, the sum of axial extents ($B_1$, $B_2$) of respective inversions of the two balloon ends are at least equal to a length of the middle, tapered balloon section (A):

$$B_1+B_2 \geq A.$$

22. The device according to claim 4, wherein the catheter tip projects by a dimension (C) past the forward fixation line (11) of the forward balloon end on the catheter shaft, preferably characterized in that the inversion depth (B) is greater than or equal to half of length (A) plus the length (C) of the projecting tip piece (18):

$$B_1=B_2 \geq A/2+C,$$

or:

$$B_1=B_2 \geq A/2+C/2.$$

23. The device according to claim 4, characterized in that, upon axial deflection of the catheter shaft toward the bowel in response to forces that typically occur during use, the catheter tip does not move more than a distance (W) beyond a first apex (8) of the forward balloon radius, and distance (W) is obtained from the distance between the first apex (8) and a second apex (20), the second apex (20) being defined as the forward intersection point of the axis (X) of symmetry with a circle of diameter (D) around a center point on the axis (X) of symmetry at the level of the attachment of the intrarectal balloon section to the catheter shaft.

24. The device according to claim 1, characterized in that, inserted in a duct (25) of the catheter shaft, or integrated into a tubing which connects the catheter shaft with a fluid container, there is a one-way element that prevents any retrograde backflow of fluid directed away from the patient through the catheter.

25. The device according to claim 24, characterized in that the one-way element in the duct (25) is a thin-walled tube element having a wall thickness of few micrometers, preferably 5 to 15 micrometers, and having the diameter of the duct (25), wherein the distal end of the tube element lies freely in the duct (25) over a length of approximately 5 to 10 mm and its proximal end is sealingly connected to the inner wall of the duct (25), thereby ensuring that the tube element opens in the presence of a flow of medium through the duct toward a tip and the tube element closes by collapsing in the presence of flow in the opposite direction.

26. The device according to claim 1, characterized in that the catheter according to the invention is configured to be an inflow catheter and is connected by a fixed tube connection (32) to a preferably bag-like container (33) for the irrigation fluid as a ready-to-use, disposal product.

27. The device according to claim 26, characterized in that the fixed tube connection (32) is equipped with a breakable seal (35) and/or with a non-return valve (36).

28. The device according to claim 4, comprising a disposable catheter, characterized in that the disposable catheter is connectable via a filling conduit (34) to a preferably reusable filling device (27), said filling device preferably being implemented as a manually operable pump balloon with a manometer indicating the balloon filling pressure.

29. The device according to claim 4, further comprising a manometer indicating the balloon filling pressure, characterized in that the manometer comprises a scale on which the filling pressure ranges required for the use of the inventive catheter are specified by suitable markings.

30. The device according to claim 4, characterized by a valve element that limits the balloon pressure and is disposed in or on a reusable filling device (27) or is integrated into a balloon filling conduit (34) of the preferably single-use catheter or into the catheter-bag unit.

31. A method for insertion of a device into the rectum or colon of a patient, said method comprising:
providing a device comprising a catheter with a catheter shaft and an inflatable balloon mounted to the catheter shaft, wherein the catheter shaft is equipped in the proximal, preanal region with at least one gripping depression (22) recessed into an outer surface of the catheter shaft, whereby to each accommodate at least one finger of the patient during insertion of the catheter into the rectum or colon of the patient, wherein a distance between the catheter tip and the at least one gripping depression is equivalent to a correct and safe insertion depth of the catheter in the rectum or colon of the patient, characterized in that the at least one gripping depression of the catheter, upon guiding the catheter in with the at least one finger of the patient, are able to restrict the movement of the catheter when the at least one finger of the patient disposed on the at least one gripping depression (22) abuts the anus, facilitating catheter insertion by a patient lacking sensitivity in the pelvic or anal region, whereby to avoid uncontrolledly deep insertion of the catheter;

gripping the catheter such that the at least one finger of the patient is disposed on the at least one gripping depression of the catheter; and inserting the catheter into the anus of the patient until the at least one finger of the patient disposed on the at least one gripping depression of the catheter abuts the anus of the patient.

32. The method according to claim 31, wherein the catheter shaft has a waist (23) in the region of its transanal placement inside the anal canal, wherein the waist (23) is positioned in a suited, distal distance from the at least one gripping depression (22), characterized in that the catheter waist (23) is snugly positioned inside the anal canal when the catheter is inserted into the rectum or colon of the patient up to a level where the at least one gripping depression (22) restricts the movement of the catheter, because the fingers accommodated in the at least one gripping depression (22) abuts the anus.

33. A device for transanally introducing an infusion into the rectum or colon of a patient, said device comprising a catheter with a catheter shaft and an inflatable balloon arranged at the catheter shaft, wherein, to ensure the most practicable and safe catheter insertion possible, with regard to an inadvertent perforation of the bowel wall due to an improper handling upon insertion of the catheter into the rectum or colon of the patient, the catheter shaft is equipped in the proximal, preanal region with one, two or more gripping depressions (22) to accommodate a user's finger each during insertion, whereby a distance between the catheter tip and the gripping depressions is equivalent to a correct and safe insertion depth of the catheter in the rectum or colon of the patient, wherein both balloon ends (6,7) taper to a shaft dimension of the catheter shaft (1) supporting the balloon (2) and are fixed to the catheter shaft (1) at a distal fixation line (11) on the one hand and at a proximal fixation line (14) on the other hand, and wherein said one, two or more gripping depressions (22) are disposed just proximally adjacent the proximal fixation line (14) of the proximal end (7) of the catheter balloon on the catheter shaft (1).

34. A device for transanally introducing an infusion into the rectum or colon of a patient, said device comprising a catheter with a catheter shaft and an inflatable balloon arranged at the catheter shaft, wherein, to ensure the most practicable and safe catheter insertion possible, with regard to an inadvertent perforation of the bowel wall due to an improper handling upon insertion of the catheter into the rectum or colon of the patient, the catheter shaft is equipped in the proximal, preanal region with one, two or more gripping depressions (22) to accommodate a user's finger each during insertion, whereby the distance between the catheter tip and the gripping depressions is equivalent to a correct and safe insertion depth of the catheter in the rectum or colon of the patient, and wherein the catheter shaft has a waist (23) in the region of its transanal placement inside the anal canal.

35. The device according to claim 34, wherein the waist (23) of the catheter shaft is positioned in a suited, distal distance from the gripping depressions (22) in the catheter shaft, ensuring that when the catheter is inserted to the level of the gripping depressions (22), the waist (23) of the catheter shaft is snugly positioned inside the anal canal.

* * * * *